United States Patent
Moeller et al.

[11] Patent Number: 6,163,158
[45] Date of Patent: Dec. 19, 2000

[54] METHOD OF AND APPARATUS FOR ASCERTAINING AT LEAST ONE CHARACTERISTIC OF A SUBSTANCE

[75] Inventors: Henning Moeller, Hamburg; Joerg Tobias, Drage/Elbe; Andreas Noack, Hamburg, all of Germany

[73] Assignee: Hauni Maschinenbau AG, Germany

[21] Appl. No.: 09/047,481

[22] Filed: Mar. 25, 1998

Related U.S. Application Data

[63] Continuation-in-part of application No. 08/799,129, Feb. 13, 1997.

[30] Foreign Application Priority Data

| Feb. 20, 1996 | [DE] | Germany | 196 06 183 |
| Aug. 20, 1997 | [DE] | Germany | 197 34 978 |

[51] Int. Cl.⁷ ............................................. G01R 27/04
[52] U.S. Cl. ................................. 324/633; 324/637
[58] Field of Search .................................. 324/636, 637, 324/633, 634, 632, 638

[56] References Cited

U.S. PATENT DOCUMENTS

| 3,783,373 | 1/1974 | Jawor | 324/58.5 |
| 4,270,083 | 5/1981 | Fitzky | 324/636 |
| 4,381,485 | 4/1983 | Steinbrecher | 324/636 |
| 4,727,311 | 2/1988 | Walker | 324/58.5 |
| 4,962,384 | 10/1990 | Walker | 343/786 |
| 5,086,279 | 2/1992 | Wochnowski et al. | 324/637 |
| 5,397,993 | 3/1995 | Tews | 324/634 |
| 5,500,599 | 3/1996 | Stange | 324/634 |
| 5,554,935 | 9/1996 | Kraszewski | 324/637 |
| 5,736,864 | 4/1998 | Moller | 324/633 |

FOREIGN PATENT DOCUMENTS

| 0 791 823 A2 | 8/1997 | European Pat. Off. . |
| 0 843 959 A1 | 5/1998 | European Pat. Off. . |
| 22 06 656 | 10/1972 | Germany . |
| 34 07 819 | 6/1985 | Germany . |
| 39 05 658 | 8/1990 | Germany . |
| 4004119C2 | 9/1993 | Germany . |

OTHER PUBLICATIONS

Hewlett–Packard, "Measuring Dielectric Constant with the HP 8510", product note 8510–3, p.4.

Measuring Dielectric Constant with the HP 8510 Network Analyzer.

*Primary Examiner*—Safet Metiahic
*Assistant Examiner*—Jimmy Nguyen
*Attorney, Agent, or Firm*—Venable; George H. Spencer; Robert Kinberg

[57] ABSTRACT

At least one characteristic, such as the mass/density and/or moisture content and/or dielectric constant, of a substance (such as the rod-like tobacco filler of a continuously advancing cigarette rod or a continuously advancing rod-like filler of filter material for tobacco smoke) is ascertained by an evaluating circuit receiving high-frequency signals from a resonator arrangement which receives microwave signals at least at two different frequencies from one or more microwave generators. The substance is caused to advance through a dielectric resonator of the resonator arrangement, and the high-frequency signals are influenced by the substance. For example, the circuit can compare first and second curves of high-frequency signals which respectively are and are not influenced by a selected substance; the curves can have sloping flanks and each of the two frequencies can be allocated to a sloping flank of a curve. The circuit compares the amplitudes of the curves to ascertain the extent of damping of the output signals due to the presence of a substance at the resonator.

51 Claims, 9 Drawing Sheets

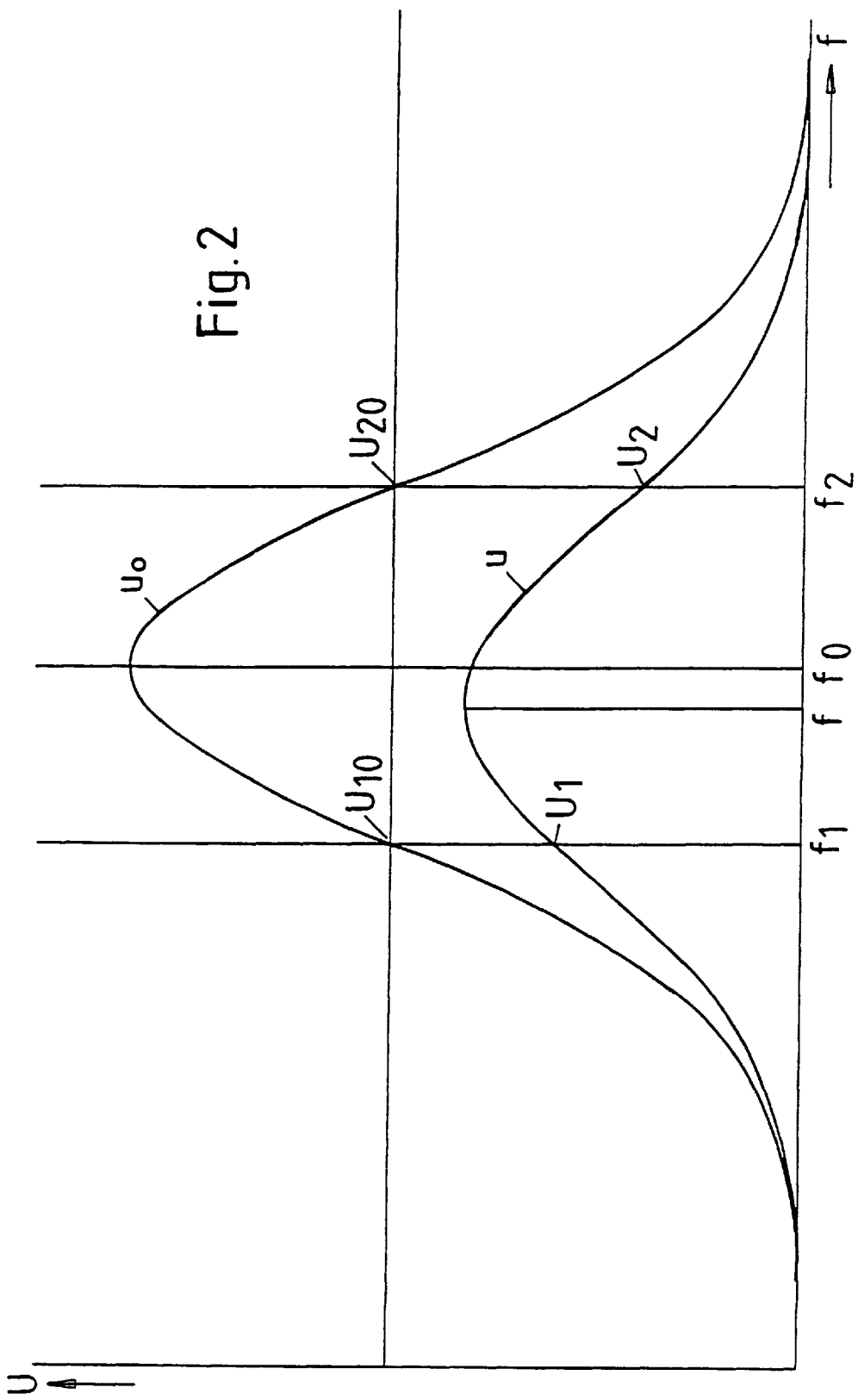

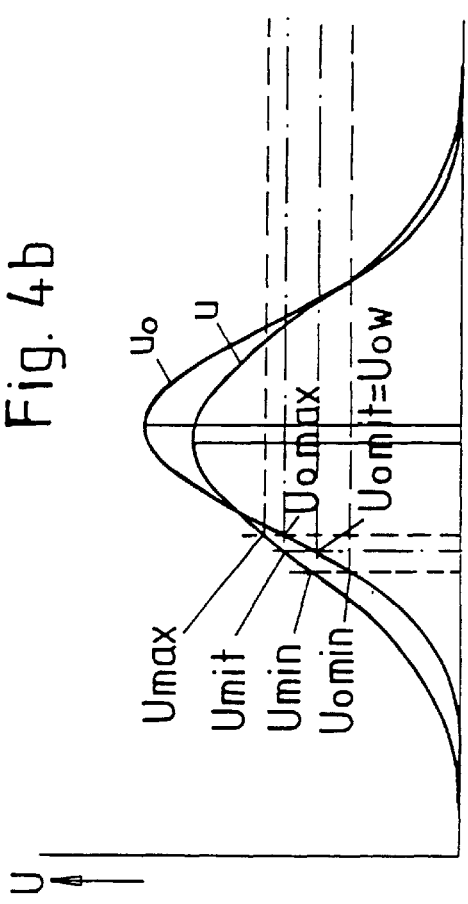

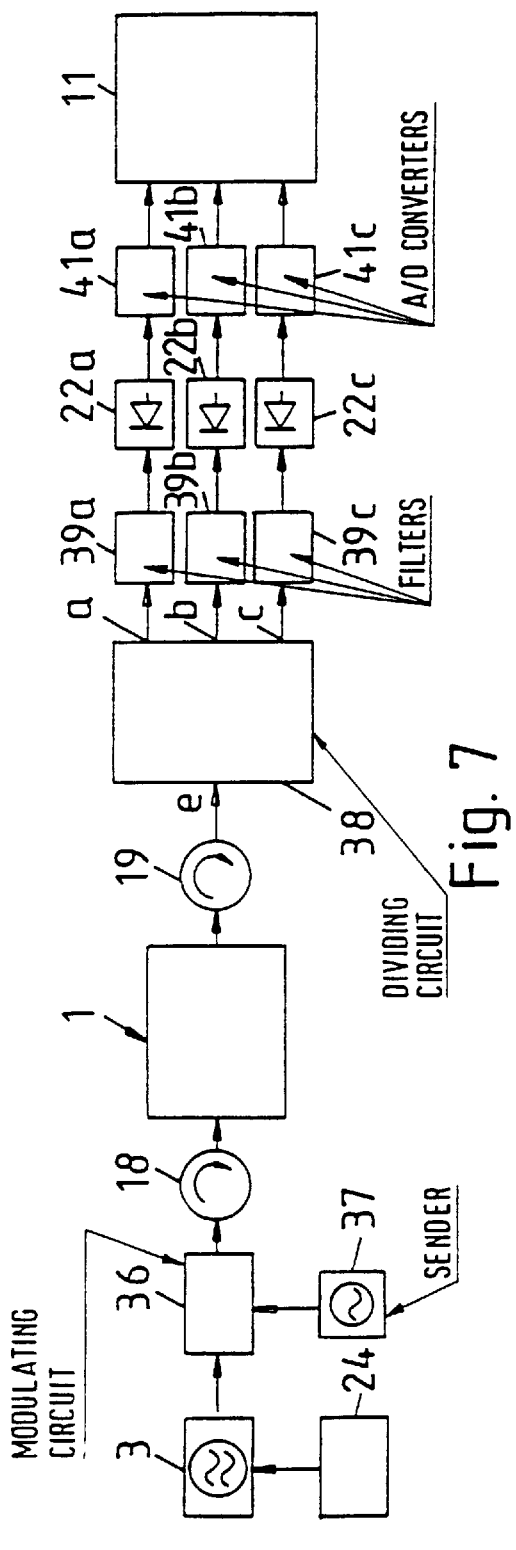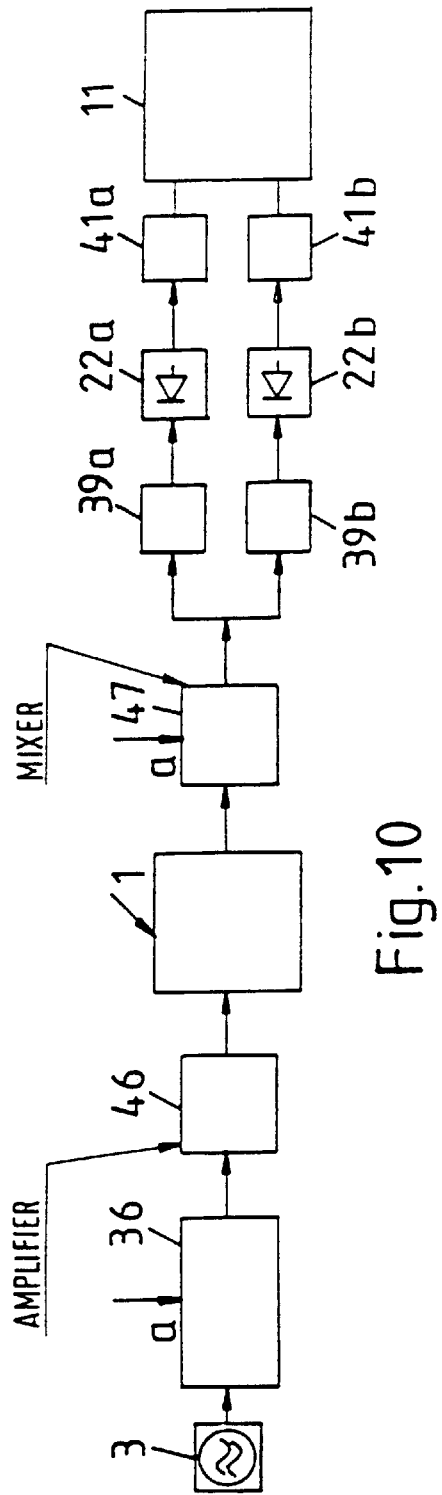

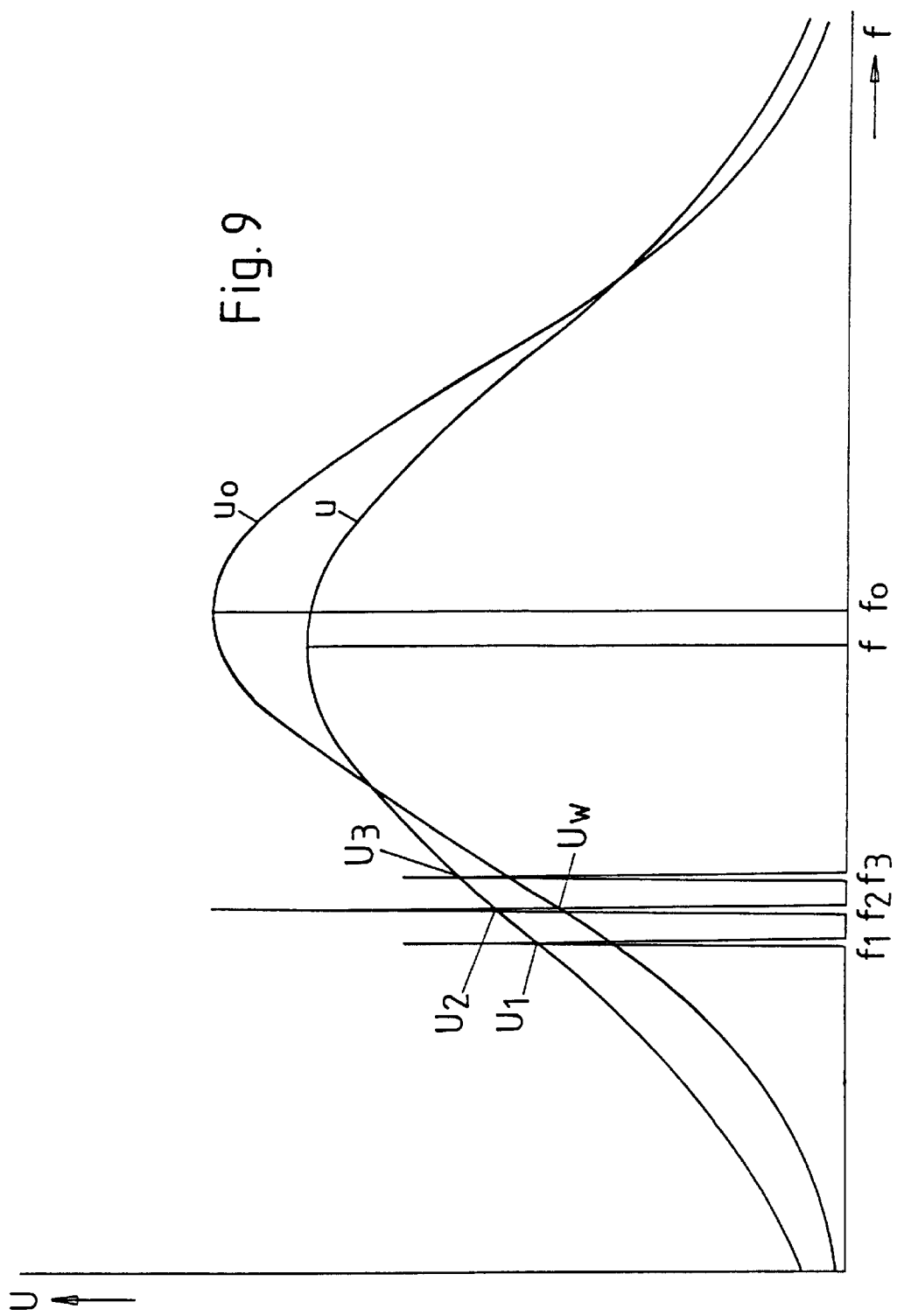

METHOD OF AND APPARATUS FOR ASCERTAINING AT LEAST ONE CHARACTERISTIC OF A SUBSTANCE

CROSS-REFERENCE TO RELATED CASE

This is a continuation-in-part of commonly owned copending patent application Ser. No. 08/799,129 filed Feb. 13, 1997 by Henning MÖLLER, Jörg TOBIAS and Andreas NOACK for "METHOD OF AND APPARATUS FOR ASCERTAINING AT LEAST ONE CHARACTERISTIC OF A SUBSTANCE".

BACKGROUND OF THE INVENTION

The invention relates to improvements in methods of and in apparatus for ascertaining one or more characteristics of certain substances, such as tobacco. More particularly, the invention relates to improvements in methods of and in apparatus for ascertaining one or more characteristics (such as the mass per unit length and/or the moisture content) of mass flows of particulate materials, such as fragments of tobacco leaf laminae and/or other smokable substances.

It is already known to ascertain certain characteristics of mass flows of tobacco particles by evaluating the extent of detuning, due to the presence of such substances, of a high-frequency resonator which receives microwaves from a suitable generator and transmits high-frequency signals to a suitable evaluating circuit. The extent of shift of the resonance frequency and damping of such high-frequency signals (in comparison with output signals which are transmitted in the absence of mass flows within the range of the high-frequency resonator) is indicative of the characteristic (s) of the material of the mass flow.

The making of smokers' products, such as plain or filter cigarettes, normally involves a testing of the mass flow of tobacco particles which are to form the rod-like fillers of such products. As a rule, the testing involves a determination of the mass of tobacco per unit length of the mass flow and/or the moisture content of the particles in the mass flow and/or the dielectric constant of tobacco (as used herein, the term "tobacco" is intended to embrace natural, reconstituted and artificial (substitute) tobacco). An accurate determination of the mass per unit length and of the moisture content is particularly important in connection with the making of cigarettes or other rod-shaped smokers' products (hereinafter referred to as cigarettes for short). For example, once the percentages of dry ingredients and moisture in a mass flow of tobacco particles are known, one can accurately determine the overall mass of the tested substance by simple addition of the signals denoting the dry mass and the moisture content. The situation is similar in connection with the processing of certain other substances such as foodstuffs, chemicals, textile materials, paper and many others.

German patent No. 40 04 119 discloses the determination of the moisture content of substances in a cavity resonator which is connected to a microwave generator. The patented apparatus resorts to a calibration curve to ascertain the resonance frequency and the half intensity width of the resonance line.

OBJECTS OF THE INVENTION

An object of the invention is to provide a novel and improved method of rapidly and accurately ascertaining one or more characteristics of various substances, such as fragments of tobacco in a mass flow of tobacco particles in a production line for the making of rod-shaped smokers' products.

Another object of the invention is to provide a method which can be resorted to for rapid and accurate determination of various ingredients (such as dry mass and/or wet mass) in mass flows of particulate materials of the type being utilized in the tobacco processing, textile, paper making, chemical, food processing and other industries.

A further object of the invention is to provide method of ascertaining one or more characteristics of mass flow of filter material for tobacco smoke.

An additional object of the invention is to provide method of rapidly and accurately ascertaining one or more characteristics (such as the percentages of solid and liquid ingredients, the total mass and/or the dielectric constant) of a rapidly advancing stream or flow of tobacco or filter material in a cigarette making machine.

Still another object of the invention is to provide a method of in line determination of one or more characteristics of smokable materials, filter materials for tobacco smoke and/ or other materials which are being conveyed in the form of mass flows or streams or rods or fillers in various plants of the tobacco processing industry.

A further object of the invention is to provide a novel and improved apparatus for the practice of the above outlined method.

Another object of the invention is to provide a machine or production line which embodies one or more apparatus for the practice of the above outlined method.

An additional object of the invention is to provide the apparatus with novel and improved means for transmitting signals to a resonator arrangement of the above outlined apparatus.

Still another object of the invention is to provide the apparatus with novel and improved means for processing signals being transmitted by the resonator arrangement of the above outlined apparatus.

A further object of the invention is to provide an apparatus which can be utilized with advantage in modern high-speed production lines for the mass-manufacture of plain or filter cigarettes, cigars, cigarillos, cheroots and/or other rod-shaped products of the tobacco processing industry.

Another object of the invention is to provide an apparatus which can be designed to accurately and rapidly ascertain one or more characteristics various substances, such as the dry mass, the moisture content, the total mass and/or the dielectric constant of tobacco particles or filter material for tobacco smoke, in cigarette makers, filter rod makers or other types of production lines.

SUMMARY OF THE INVENTION

One feature of the present invention resides in the provision of a method of ascertaining at least one characteristic of a substance by resorting to a high-frequency resonator arrangement which is detuned in the presence of the substance. The method comprises the steps of supplying or transmitting to an input of the resonator arrangement microwaves having at least two different frequencies whereby an output of the resonator arrangement respectively furnishes or transmits first and second curves of high-frequency output signals in the presence and absence of a substance at the resonator arrangement. Such curves have different amplitudes, and the method further comprises the step of evaluating the output signals including comparing the curves to ascertain shifts of resonance frequencies of the output signals due to the presence of a substance at the resonator arrangement and comparing the amplitudes of the curves to ascertain damping of output signals due to the presence of a substance at the resonator arrangement.

The supplying step can include continuously transmitting to the input of the resonator arrangement microwaves having at least two different frequencies.

The method can further comprise the step of periodically varying the frequencies of microwaves which are being transmitted to the input of the resonator arrangement. This varying step can include repeatedly shifting between higher and lower frequency values. Such varying step can also include repeatedly and continuously wobbling between higher-frequency and lower-frequency values. The frequencies of the microwaves can be allocated to a sloping flank of a curve of high-frequency output signals. The wobbling step can involve substantially sinusoidally wobbling the frequencies of the microwaves between threshold values with relatively small frequency changes or differences. The output signals can have d-c fractions and substantially sinusoidally varying a-c fractions. The evaluating step of such method can comprise transmitting the d-c fractions and the a-c fractions to discrete calculating or computing stages, polynomially computing the fractions in the respective stages with constants to thus generate partial signals, and adding or summing the partial signals. Such evaluating step can further comprise ascertaining the constants by parameterization on the basis of reference values of the substance; such reference values can include—as a function of the at least one characteristic to be ascertained in accordance with the novel method—at least one of the density/mass, moisture content and dielectric constant of the substance being tested.

The aforementioned threshold values can be at least substantially symmetrical with reference to an inversion point of a downwardly sloping flank of a curve.

The at least two different frequencies of microwave signals can be symmetrical with reference to a resonance frequency which is not influenced by the substance being tested, and the at least two different frequencies can be allocated to downwardly sloping flanks of a resonance curve.

The method can further comprise the step of generating the microwaves, and such step can include substantially sinusoidally modulating the amplitude of a microwave oscillation at a relatively low frequency. The modulating step can include maintaining the basic frequencies of the developing frequency bands at a downwardly sloping flank of the curve, preferably or particularly at an inversion point of such flank.

The supplying step can also include transmitting to the input of the resonator arrangement microwaves at two modulation-established frequencies, and the evaluating step of such method can comprise scaling down the microwave frequencies and selectively filtering those frequency ranges which influence the shifts of resonance frequencies and the damping of the output signals.

The substance can consist of or it can contain tobacco, and the at least one characteristic to be ascertained is or can be the mass/density of tobacco.

The substance to be tested can be tobacco in a tobacco particle flow, and the at least one characteristic to be tested can be the moisture content/mass of tobacco. The substance to be tested can contain or can constitute tobacco in a flow of shredded and/or otherwise comminuted (cut) tobacco particles, and the at least one characteristic to be ascertained can be the dielectric constant of cut or comminuted or shredded tobacco.

Another feature of the invention resides in the provision of an apparatus for ascertaining at least one characteristic of a substance (e.g., tobacco). The apparatus comprises a resonator arrangement, and means for supplying to an input of the resonator arrangement microwave signals at least at two different frequencies. The resonator arrangement has output means for the transmission of first and second high-frequency signals which are respectively generated in the presence and in the absence of a substance to be tested at the resonator arrangement, and the apparatus further comprises means for evaluating the first high-frequency signals. The evaluating means comprises means for comparing first and second resonance curves having different amplitudes and respectively denoting the first and second high-frequency signals to thus ascertain shifts of resonance frequency attributable to the presence of a substance to be tested at the resonator arrangement, and means for comparing the amplitudes of the first and second resonance curves to thus ascertain the damping of such amplitudes by a substance to be tested.

The means for supplying microwave signals can include at least one microwave generator which is designed to uninterruptedly transmit to the input of the resonator arrangement microwave signals at the at least two different frequencies. The generator can include means for periodically altering the frequency of the microwave signals.

The means for supplying microwave signals can be designed in such a way that it comprises a microwave generator which is connected to the input of the resonator arrangement and a frequency regulator which is connected with the microwave generator to periodically vary the frequency of signals from the microwave generator between higher and lower values.

Alternatively, the means for supplying microwave signals can comprise a microwave generator which is connected to the input of the resonator arrangement and a frequency regulator which is connected with the generator to continuously and regularly vary the frequency of signals from the generator between higher and lower values.

The at least two different frequencies can be symmetrical to each other with reference to a resonance frequency of the second curve and are located at downwardly sloping flanks of the second curve.

It is also possible to design the means for supplying microwave signals in such a way that it comprises a microwave generator connected to the input of the resonator arrangement and a frequency regulator connected with the generator to continuously and regularly vary the frequency of signals from the generator between higher and lower values. The microwave signals are allocated to downwardly sloping flanks of at least one of the curves. The frequency regulator can be arranged to substantially sinusoidally vary the frequency of signals from the microwave generator. The comparing means of the evaluating means can comprise means for ascertaining d-c and a-c fractions of the first high-frequency signals.

The means for supplying microwave signals can include means for transmitting to the input of the resonator arrangement microwaves at frequencies having upper and lower threshold values and continuously wobbling between such values. The threshold values are at least substantially symmetrical to each other with reference to an inversion point of a downwardly sloping flank of a resonance curve.

The evaluating means can comprise calculating or computing circuits or stages which respectively receive d-c fractions and a-c fractions of the high-frequency signals and include means for polynomially computing or calculating the fractions with constants to thus generate partial signals, and means for summing or adding such partial signals. Such evaluating means can further comprise means for ascertaining the constants by parameterization on the basis of reference values of a substance. The reference values can include—as a function of the at least one characteristic to be ascertained by the improved apparatus—at least one of the density/mass, moisture content and dielectric constant of the substance to be tested.

The means for supplying microwave signals can also comprise means for substantially sinusoidally modulating the frequencies of the microwave signals with a relatively low frequency. Bands of modulated frequencies can include a basic frequency at a downwardly sloping flank of the resonance curve, particularly or preferably at an inversion point of such curve.

The resonator arrangement can comprise a preferably metallic housing having an inlet and an outlet for a flow of a substance to be tested (e.g., a tobacco stream). The housing can be dynamically balanced; for example, such dynamically balanced housing can include or constitute a cylinder. The resonator arrangement can further comprise at least one dielectric resonator in the housing, and such resonator can provide a path for the advancement of a substance (e.g., a cigarette rod) between the inlet and the outlet of the housing. The resonator arrangement can further comprise a tubular guide for the substance, and such guide can include portions at the inlet and at the outlet of the housing. A presently preferred guide extends through the at least one dielectric resonator. The just described resonator arrangement can further comprise conductive sleeves which surround the guide in the regions of the inlet and the outlet of the housing; such sleeves can contain or they can consist of a metallic material.

Alternatively, the resonator arrangement of the improved apparatus can comprise two resonators each of which receives microwave signals from the supplying means, one of which transmits the aforementioned high-frequency signals, and the other of which transmits to the evaluating means additional signals which are influenced by a reference substance to compensate for disturbances. Such resonator arrangement can further comprise at least substantially identical housings for the two resonators.

The at least one characteristic which is to be ascertained by the improved apparatus can be the density/mass of tobacco or the moisture content of cut tobacco in a cigarette rod or the dielectric constant of cut tobacco, particularly in a cigarette rod.

A further feature of the invention resides in the provision of a method of ascertaining at least one characteristic of a substance by means of a high-frequency resonator arrangement which is detuned in the presence of the substance to be tested. This method comprises the steps of supplying to an input of the resonator arrangement microwaves having two frequencies whereby an output of the resonator arrangement respectively furnishes first and second curves of high-frequency output signals in the presence and absence of a substance (the curves have amplitudes and sloping flanks and each of the two frequencies is allocated to a sloping flank of a curve), and evaluating the output signals including comparing the curves to ascertain shifts of resonance frequencies of the output signals due to the presence of a substance, and comparing the amplitudes of the curves to ascertain damping of output signals due to the presence of a substance. The just outlined method can further comprise the step of periodically varying the frequencies of the microwaves which are supplied to the input of the resonator arrangement, and the varying step of such method can include repeatedly switching between higher and lower frequency values.

Still further, the just outlined method can comprise the step of modulating the frequencies of the microwaves with a lower-frequency rectangular a-c voltage. The output signals can constitute d-c signals and the method can further comprise the steps of ascertaining those d-c signals which are transmitted by the output of the resonator arrangement at the minimum and maximum values of the modulated frequencies, and processing the thus ascertained maximal and minimal signals into evaluation signals. The processing step can include providing a further signal which denotes the sum of the maximal and minimal signals and processing the further signal into a signal denoting an average value of the maximal and minimal signals. Such processing step can further include providing an additional signal which denotes the difference between the maximal and minimal signals, transmitting the further and additional signals to discrete calculating stages, polynomially computing the maximal and minimal signals in the respective stages with constants to thus generate partial signals, and adding (summing up) the partial signals. Such method can further comprise the step of ascertaining the aforementioned constants by parameterization on the basis of those reference values of the substance which are to be ascertained. Such reference values can include the density/mass, the moisture content and the dielectric constant of the substance to be tested.

The substance to be tested can be tobacco, and the at least one characteristic can be the mass/density of tobacco. For example, the substance can constitute a rod-like filler of cut tobacco. Alternatively, the at least one characteristic can be the moisture content of tobacco, for example, the moisture content of successive increments of a rod-like filler of cut tobacco.

Still another feature of the invention resides in the provision of an apparatus for ascertaining at least one characteristic of a substance. The apparatus comprises a resonator arrangement, means for supplying to an input of the resonator arrangement microwave signals at two frequencies (the resonator arrangement has output means for the transmission of first and second high frequency signals which are respectively generated in the presence and in the absence of a substance at the resonator arrangement), and means for evaluating the first high-frequency signals. The evaluating means comprises means for comparing first and second resonance curves having amplitudes and sloping flanks. Each of the frequencies is allocated to a sloping flank of a curve and the first and second curves respectively denote the first and second high-frequency curves to thus ascertain shifts of resonance frequencies attributable to the presence of a substance at the resonator arrangement. The evaluating means further comprises means for comparing the amplitudes of the first and second resonance curves to thus ascertain the damping of such amplitudes by a substance.

The supplying means of the just discussed apparatus can comprise a microwave generator which is connected to the input, and a frequency regulator which is connected with the generator to periodically vary the frequency of signals from the generator between higher and lower values.

The apparatus can further comprise means for modulating the frequencies of the microwaves with a lower-frequency rectangular a-c voltage. The first and second high-frequency signals can constitute d-c signals, and the modulated frequencies have maximum and minimum values. The apparatus can further comprise means for ascertaining the d-c signals which are transmitted by the output means of the resonator arrangement at the minimum and maximum values of the modulated frequencies, and means for evaluating the ascertained signals into evaluation signals. The evaluating means can comprise summing and subtracting circuits having outputs for signals which are transmitted to discrete calculating stages having means for polynomially computing signals from the respective (summing, subtracting) circuits with constants to thus generate partial signals. Such evaluating means can further comprise means for adding (totalizing) the partial signals as well as means for ascertaining the aforementioned constants by parameterization on the basis of reference values of a substance. The reference values can include (as a function of the at least one characteristic to be ascertained) at least one of density/mass, moisture content and dielectric constant of the substance.

The resonator arrangement can comprise a metallic housing having an inlet and an outlet for the flow of a substance to be tested, such as a tobacco stream. The housing is or can be dynamically balanced and can include a cylinder. The resonator arrangement can comprise at least one dielectric resonator in the housing.

In accordance with one presently preferred embodiment, the at least one characteristic is the density/mass of tobacco and/or the moisture content of cut tobacco in a cigarette rod.

The novel features which are considered as characteristic of the invention are set forth in particular in the appended claims. The improved apparatus itself, however, both as to its construction and the mode of assembling, installing and utilizing the same, together with numerous additional important features and advantages thereof, will be best understood upon perusal of the following detailed description of certain presently preferred specific embodiments with reference to the accompanying drawings.

BRIEF DESCRIPTION OF THE DRAWINGS

FIG. 2 is a coordinate system showing the resonance curves of a resonator arrangement in the apparatus of FIG. 1, one curve being indicative of the output signals when the dielectric resonator of the resonator arrangement is not influenced and the other curve being indicative of the output signals when the resonator is influenced by a substance to be tested;

FIGS. 4a, 4b and 4c illustrate coordinate systems wherein the curves denote the high-frequency signals transmitted by the resonator arrangement in the apparatus of FIG. 3;

FIG. 7 is a diagrammatic view of a third apparatus wherein the evaluating circuit receives three signals having frequencies obtained as a result of modulation of a microwave signal;

FIG. 9 is coordinate system similar to that of FIG. 2 but showing curves denoting the signals transmitted by the output means of the resonator arrangement in the apparatus of FIG. 7;

FIG. 10 is a diagrammatic view similar to that of FIG. 1 but showing the details of still another apparatus with different means for transmitting microwave signals to the resonator arrangement and with different means for transmitting high-frequency signals to the evaluating circuit.

DESCRIPTION OF PREFERRED EMBODIMENTS

Figure 1:
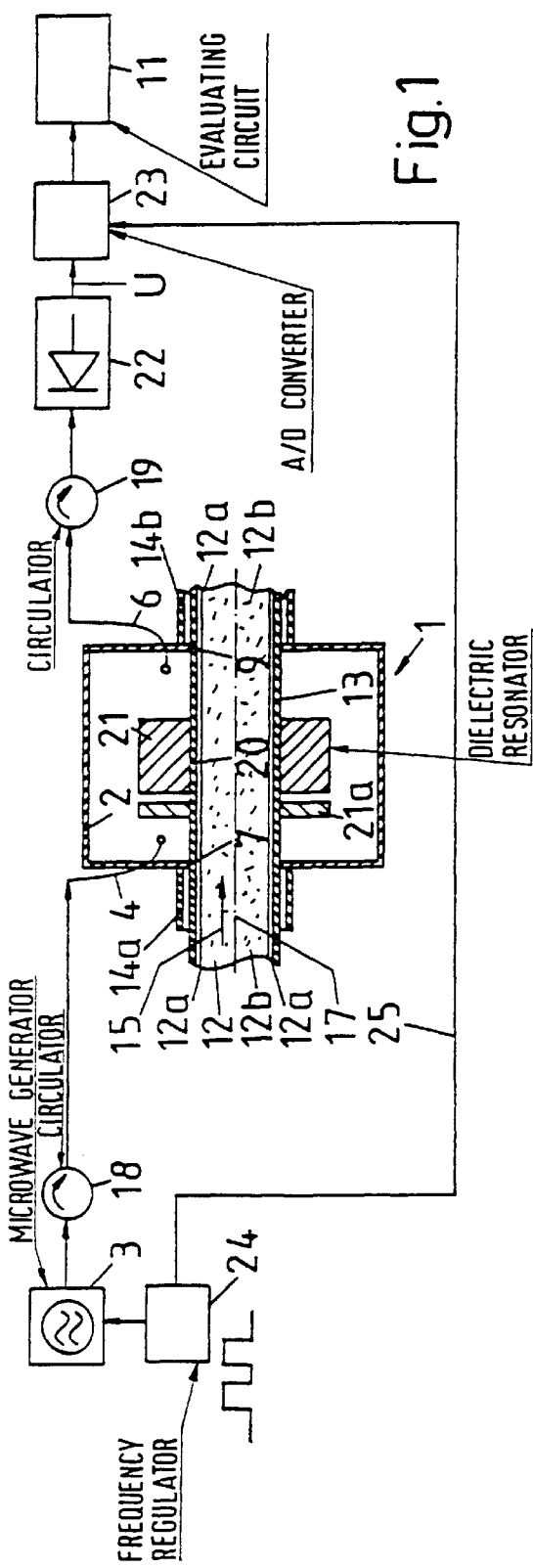
FIG. 1 is a diagrammatic partly elevational and partly sectional view of an apparatus which is designed to ascertain one or more characteristics of a continuous cigarette rod and is constructed and assembled in accordance with a first embodiment of the invention.

Referring first to FIG. 1, there is shown an apparatus which is designed to ascertain at least one characteristic of a substance (tobacco) forming a rod-shaped filler 12b in a tubular envelope 12a of a continuous rod 12, e.g., a rod containing fragments of tobacco leaf laminae in a cigarette paper wrapper and being ready to be subdivided into plain cigarettes of unit length or multiple unit length. For example, the making of the rod 12 can take place in a machine known as PROTOS 100 which is distributed by the assignee of the present application. PROTOS 100 is a high-performance production line with an output of 11000 cigarettes per minute or more.

The apparatus of FIG. 1 comprises a high-frequency resonator arrangement 1 including a dielectric resonator 21 in a housing 2 which is dynamically balanced and can constitute a cylinder. The illustrated housing 2 is made of a conductive metallic material, such as copper. It is equally possible to employ other types of rotationally symmetrical housings or housings having a polygonal cross-sectional outline and made of a material other than copper or other than a metallic material.

The resonator arrangement 1 receives high-frequency signals (preferably microwave signals) from a source 3 (such as a generator) by way of a first conventional coaxial cable 4, and a second conventional coaxial cable 6 is employed to connect the output of the resonator arrangement 1 with an evaluating arrangement 11. The cables 4 and 6 are provided with customary coupling loops, not shown in FIG. 1.

The resonator 21 is made of a dielectric material, such as a ceramic or a synthetic plastic substance having a high dielectric constant (for example, the resonator can be made of $BaO$—$PbO$—$Nd_2O_3$—$TiO_2$). This resonator is a hollow cylinder which is fixed in the housing 2 by resorting to suitable distancing or spacer means, not shown. A portion 21a of the resonator 21 is movable axially of the other portion or portions, e.g., for the purpose of ascertaining and/or adjusting (selecting) the resonance frequency. An advantage of a dielectric resonator is that it contributes to higher sensitivity and greater accuracy of measurements.

The housing 2 is provided with an inlet 7 and an outlet 9. This renders it possible to insert a tubular guide 13 which defines a path for the advancement of the cigarette rod 12 in the direction which is indicated by an arrow 15. The apparatus of FIG. 1 is designed to ascertain the dry mass and/or the wet mass and/or the overall mass or the dielectric constant of the filler 12b. The guide 13 is made of a non-conductive material, such as quartz. One of the functions of the guide 13 is to prevent undesirable foreign matter (such as dust and small particles of tobacco) from penetrating into the housing 2; foreign matter in the housing could interfere with proper operation of the resonator arrangement 1. Tubular sleeves 14a and 14b surround the guide 13 in the region of the inlet 7 and outlet 9 to prevent the radiation of excessive quantities of the high-frequency field from the housing 2 by way of the inlet and/or outlet. The sleeves 14a and 14b are preferably made of a conductive material, e.g., a suitable metallic material.

The axis 17 of the resonator 21 preferably coincides with the axes of the guide 13 and housing 2; such symmetrical arrangement of these parts also contributes to the accuracy and reliability of the measurements. The sensitivity of the measurements is further enhanced due to the fact that the guide 13 extends through the central opening 20 of the resonator 21; such positioning of the parts 13 and 21 relative to each other has been found to greatly enhance the sensitivity as well as the accuracy of the determination of one or more parameters of the filler 12b in the cigarette rod 12.

The cable 4 supplies to the dielectric resonator 21 two microwave signals having different frequencies in the GHz range, e.g., approximately 6 GHz. A conventional circulator 18 is employed to prevent a feedback from the resonator arrangement 1 to the microwave generator 3. FIG. 2 shows that the cable 4 supplies microwave signals having frequencies f1 and f2 which are symmetrical to each other with reference to the resonance frequency fo (note the curve uo of FIG. 2 denoting the resonance frequency of the housing 2 when the guide 13 is empty). The microwave generator 3 is controlled by a frequency regulator 24 which causes the generator 3 to periodically shift from the transmission of signals having the lower frequency f1 to the transmission of signals having the higher frequency f2, back to the transmission of lower-frequency signals, and so forth.

It is also possible to employ two microwave generators in lieu of the single generator 3; the two generators are then designed to transmit signals having slightly or somewhat different frequencies, and a modified frequency regulator then causes the two generators to alternately supply different-frequency signals via cable 4 and on to the high-frequency resonator arrangement 1. For example, the regulator which is used in conjunction with two generators can be set up to turn off one of the generators when the other generator is on, to thereupon shut off the other generator while turning on the one generator, and so forth.

It is equally possible to supply (wobble) microwave signals which are frequency modulated symmetrically relative to the resonance frequency fo and to employ for the measurement only those signals which exhibit the frequencies f1 and f2.

The cable 6 transmits output signals from the resonator arrangement 1, by way of a (feedback preventing) circulator 19 and on to a microwave diode 22. For example, the diode 22 can be that known as Type HP 8472B which is distributed by Hewlett-Packard, Herrenberger Strasse 130, D-71034 Böblingen, Federal Republic Germany. The purpose of the diode 22 is to convert the microwave signals into d-c signals. The signals U at the output of the diode 22 are represented by the curve uo of FIG. 2 when the guide 13 is empty, and by the curve u when the guide 13 contains an advancing cigarette rod 12.

Since the frequencies f1 and f2 are symmetrical with reference to the resonance frequency fo, the signals U10 and U20 which are transmitted by the diode 22 are identical, i.e., the difference between the signals U10 and U20 (as measured along the ordinate in the coordinate system of FIG. 2) is zero. Such situation prevails when the guide 13 is empty. When the apparatus of FIG. 1 is in use (i.e., when a cigarette rod 12 or any other body to be tested in caused to advance through the guide 13), the values of the resonance frequency f are reduced and, furthermore, the amplitude is also reduced (reference should be had to the curve u of FIG. 2). At the frequencies f1 and f2, the diode 22 then transmits signals U1 and U2 having different values (as measured along the ordinate). The difference between the signals U1 and U2 is dependent on the extent of shift of resonance frequency, i.e., it increases in response to an increase of such shift. An evaluation of the signals at the frequencies f1 and f2 renders it possible to ascertain the extent of damping and the extent of shift of resonance frequency. Thus, and the same as in connection with other types of high-frequency measurements, the evaluating arrangement 11 can ascertain the mass/density ratio (independently of the moisture), the moisture (independently of the density) as well as the dielectric constant. If the corresponding signals are added up (summed), one can ascertain the total mass including the dry mass and the wet mass.

The connection between the output of the diode 22 and the input of the evaluating arrangement 11 comprises an analog-to-digital (A/D) converter 23 (e.g., a circuit known as Type MX 7672-03 distributed by Maxim Integrated Products, 120 San Gabriel Drive, Sunnyvale, Calif. 94086). The circuit 23 digitalizes the signals from the diode 22 and further serves as a gate circuit which permits the signals from the diode 22 to reach the input of the evaluating arrangement 11 when it receives a corresponding signal from the frequency regulator 24 via conductor means 25. The regulator 24 applies to the microwave generator 3 voltage impulses of different intensities, and such signals influence the frequencies of signals which are being transmitted via coaxial cable 4. As already explained above, the arrangement can be such that the generator 3 is caused to shift from the transmission of signals having a lower frequency f1 to the transmission of signals having a higher frequency f2, thereupon back to the transmission of signals having the frequency f1, and so on.

In order to exclude transitional phenomena, the A/D converter 23 receives signals to connect the output of the diode 22 with the input of the evaluating arrangement 11 only when the resonator arrangement 1 actually receives (via cable 4) a signal having the frequency f1 or a signal having the frequency f2.

Figure 3:
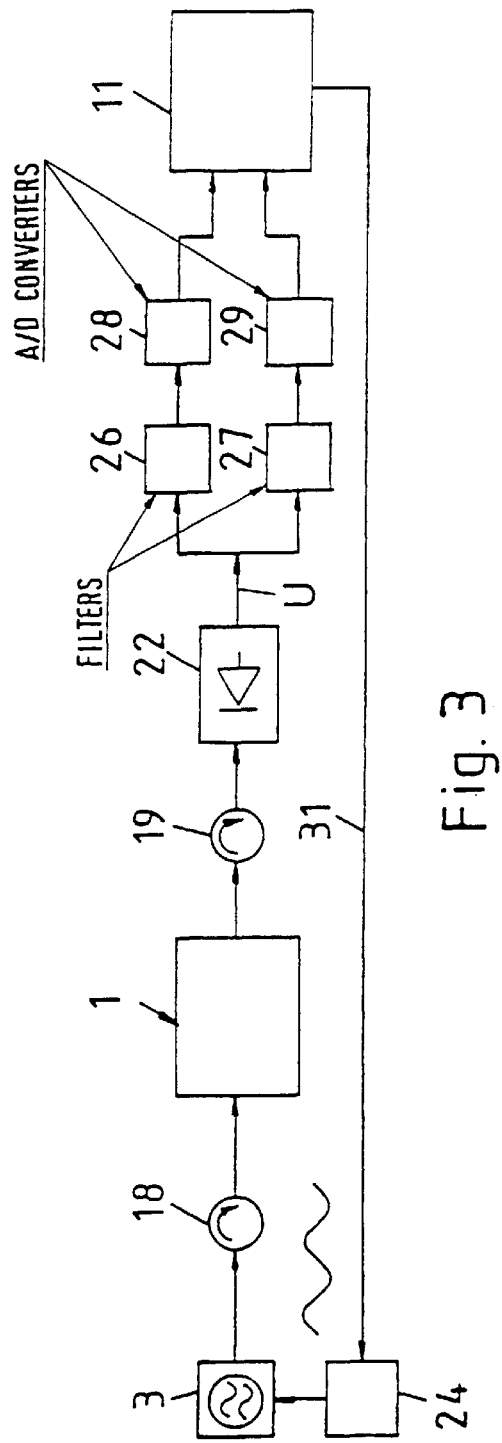
FIG. 3 is a view similar to that of FIG. 1 but showing certain details of a modified apparatus wherein the resonator arrangement receives wobbled microwave signals.

FIG. 3 illustrates a modified apparatus. Those component parts of the modified apparatus which are identical with or clearly analogous to the corresponding component parts of the apparatus of FIG. 1 are denoted by similar reference characters. The microwave generator 3 is again designed to transmit microwave signals having a frequency in the GHz region (e.g., about 6 GHz). A frequency regulator 24 is operatively connected with and causes the generator 3 to periodically vary the frequency of output signals in a sinusoidal fashion. This can be readily seen in FIG. 4a wherein the curve s denotes the changes of frequency f as a function of time t. The average frequency fm (for example, several hundred KHz) is continuously varied sinusoidally (as indicated by the curve s) within a frequency range Δf. As shown in FIG. 4b, the average frequency fm is preferably at the inversion point Uow of the resonance curve uo which has been determined while the housing 2 of the resonator arrangement 1 was empty. The output signal U of the diode 22, which receives signals from the generator 3 via circulator 18, resonator arrangement 1 and circulator 19 fluctuates between the values Uomin and Uomax when no tobacco is caused to pass through the housing 2 of the resonator arrangement 1. In actual use, i.e., when a filler 12b or another flow of fibrous material of the tobacco processing industry is caused to advance through the dielectric resonator in the housing of the resonator arrangement 1 of FIG. 3, the progress of the damping curve is that shown in FIG. 4b, as at u, which exhibits the values Umin and Umax. The reference characters Uomit and Umit denote average values which are available at the average frequency fm. In FIG. 4b, the reference character fo again denotes the resonance frequency when the housing of the resonator arrangement of FIG. 3 is empty, and the character f denotes the resonance frequency when the apparatus of FIG. 3 is in actual use.

The coordinate system of FIG. 4c shows the variations of the signals U at the output of the diode 22 of FIG. 3 as a function of time. When the apparatus of FIG. 3 is not in actual use, the corresponding curve includes a d-c fraction Uog and an a-c fraction Uoa; however, the curve has a d-c fraction Ug and an a-c fraction Ua when the apparatus is in actual use.

FIG. 3 shows that the signals at the output of the diode 22 are transmitted to a d-c fraction filter 26 and to an a-c fraction filter 27. The two filters 26 and 27 respectively transmit signals to A/D converters 28 and 29 wherein the corresponding signals are digitalized prior to being transmitted to the corresponding inputs of the evaluating arrangement 11. The latter can transmit (via conductor means 31) to the frequency regulator 24 suitable correction signals as soon as the average frequency fm migrates beyond the inversion point of the resonance curve uo shown in FIG. 4b. Such correction via conductor means 31 causes the frequency fm of the output signal from the generator 3 to reassume the value Uow which corresponds to the inversion point of the resonance curve Uo.

Based on a comparison between the d-c fractions Uog and Ug, as well as between the a-c fractions Uoa and Ua (when the housing 2 respectively does not contain a filler 12b and contains such a filler), the evaluating arrangement 11 can draw conclusions regarding the characteristics of tobacco (such as its wet mass, its dry mass and/or is dielectric constant). This will be explained in detail with reference to FIGS. 5 and 6.

Figure 5:
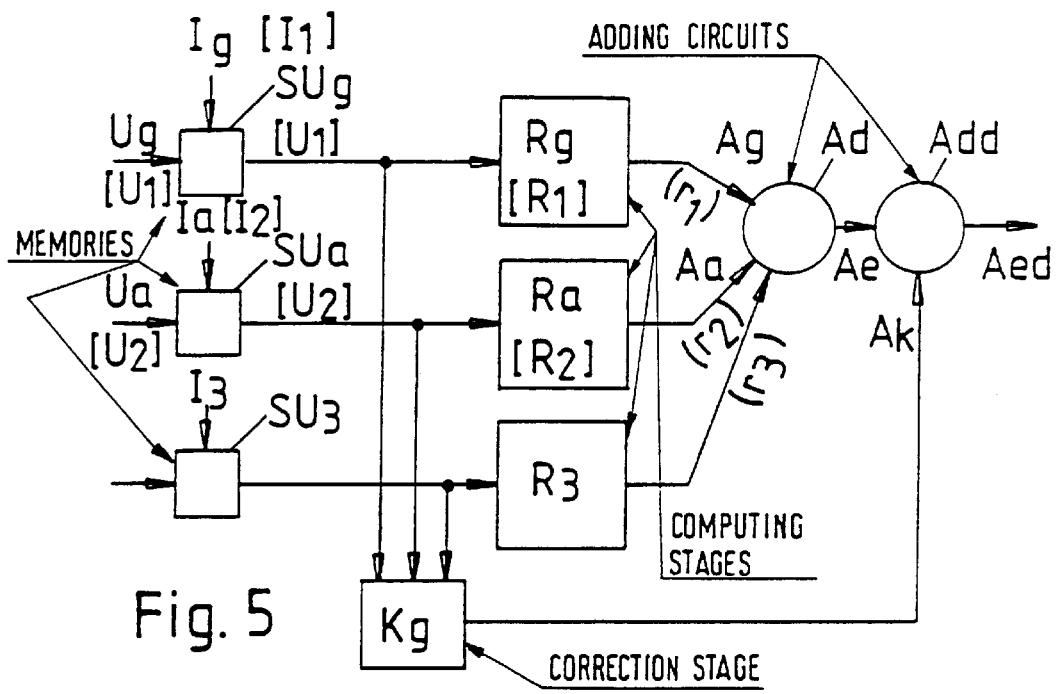
FIG. 5 is a diagrammatic view of an evaluating circuit which can be utilized to ascertain the dry mass and/or the wet mass of successive increments of a rod-like tobacco filler which is confined in the tubular envelope of a continuous cigarette rod.

FIG. 5 shows schematically the processing of the signals Ua, Ug (see FIG. 4c) in the evaluating arrangement 11 of the apparatus which is shown in FIG. 3 for the purpose of ascertaining the mass/density values. In the following description, the signal Ua is intended to denote the d-c value of the a-c fraction shown in FIG. 4c. The first step involves the storage of digitalized signals in the memories SUg and SUa which are shown in FIG. 5. Such signals are addressed by a scanner in a sequence corresponding to predetermined increments of the cigarette rod 12, e.g., increments each having a length of 1 mm. This means that, if the cigarette rod 12 is advanced at a rate required to turn out 10000 plain cigarettes of unit length (60 mm) per minute, the addressing or scanning frequency is 100 microseconds. In other words, the memories SUg and SUa are addressed at intervals of 100 microseconds. The duration of the pulses Ig and Ia of transmission of signals (values) from the memories SUg and SUa to the calculating stages Rg and Ra, respectively, of the evaluating arrangement 11 is even less. In the stages Rg and Ra, the transmitted signals are processed with constants to furnish output values Ag and Aa, respectively. In a simple case, the processing of signals in the stages Rg and Ra can be carried out with polynomials of the type a+b Ug=Ag and c+d Ua=Aa, respectively. The constants a, b, c and d are ascertained by resorting to parameterizing, namely by measuring the values Ug and Ua of cigarettes which were weighed to accurately ascertain their masses/densities. The relationships between different masses/densities and the corresponding values of Ug and Ua render it possible to ascertain the aforementioned constants.

In principle, it is equally possible to resort to polynomials of a higher order or to other types of functions.

The signals Ag and Aa at the outputs of the respective calculating stages Rg and Ra are transmitted to the corresponding inputs of a first adding or summing circuit or stage Ad, and the signal Ae at the output of the circuit Ad is indicative of the density/mass. If the intensity and/or other characteristic(s) of the signal Ae departs or depart from the desired or required characteristic or characteristics, a correction stage Kg can be utilized to transmit an empirically determined correction signal Ak to the corresponding input of a second adding or summing circuit or stage Add which processes the signals Ae and Ak to furnish an output signal Aed which is even more accurately representative of the density/mass value of the filler 12b in the tested cigarette rod 12.

The evaluation of signals in the arrangement 11 of the apparatus which is shown in FIG. 1 can be carried out in a manner analogous to the just described mode of operation of the arrangement 11 in the apparatus of FIG. 3. The signals furnished by the A/D converter 23 of FIG. 1 are stored in memories corresponding to the memories SUg, SUa of FIG. 5.

The evaluation with the evaluating circuit arrangement of FIG. 5 can also be realized by employing a third memory SU3. The memories SUg=SU1 and SUa=SU2 receive the signals U1, U2 (FIG. 7). The calculating stages are denoted by the characters R1, R2, R3 and the signals at the outputs of these stages are respectively shown at r1, r2 and r3. The transmission or transfer pulses are respectively shown at I1, I2 and I3.

Basically, an evaluation of high-frequency measurement signals for the purpose of ascertaining the moisture content of tobacco in a cigarette rod can be carried out in the same way as already described hereinabove. The difference is that, in lieu of utilizing cigarettes having a known weight/mass, the parameterization involves the utilization of cigarettes having certain known moisture quantities or percentages, i.e., various values of relative moisture.

Figure 6:
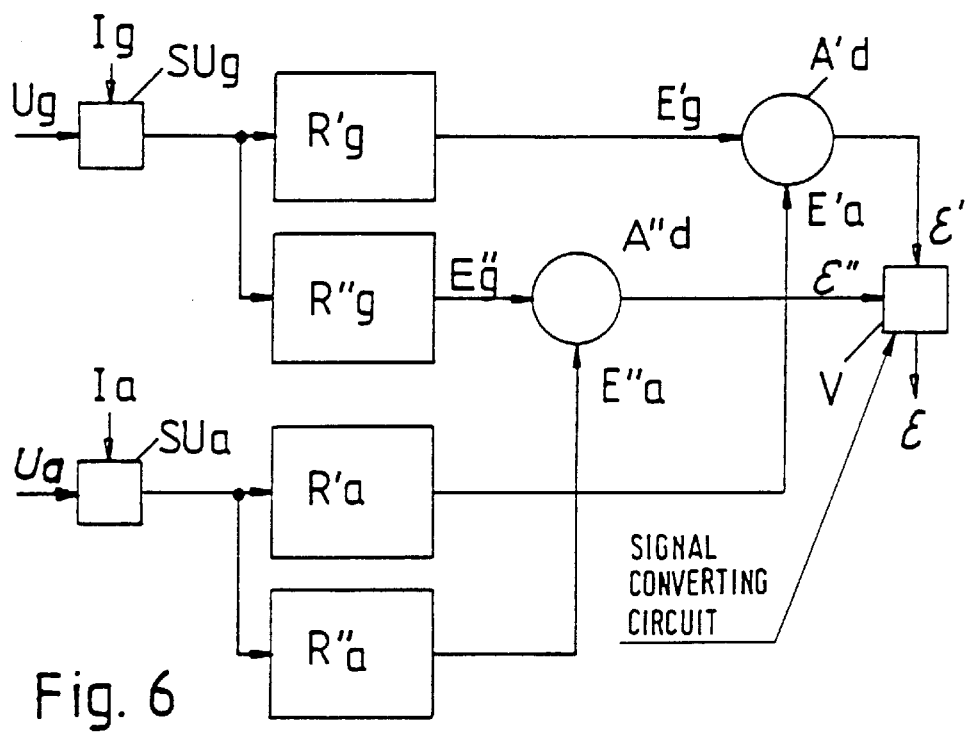
FIG. 6 is a diagrammatic view of an evaluating circuit which is utilized to furnish signals denoting the dielectric constants of successive increments of a flow of tobacco particles.

FIG. 6 shows schematically the processing (evaluation) of signals Ua, Ug (reference should be had again to FIGS. 4a, 4b and 4c) in an evaluating circuit 11 of the type utilized in the apparatus of FIG. 3 for the purpose of ascertaining the dielectric constant ∈ of the tobacco filler 12b in the cigarette rod 12. The first step involves temporary storage of the signals Ug and Ua in the memories SUg and SUa. As already described with reference to FIG. 3, memories SUg and SUa are addressed periodically and at relatively short time intervals, i.e., the contents of these memories are transmitted by transmission or transfer impulses Ig and Ia to selected calculation or computing stages. As shown, the real portion of the information stored in the memory SUg is transmitted to the stage R'g and the imaginary portion of such information is transmitted to the stage R"g. Analogously, the real portion of the information obtained in the memory SUa is transmitted to the stage R'a, and the imaginary portion of such information is transmitted to the stage R"a. The stages R'g and R'a process the real portions with constants into output signals E'g E'a, and stages R"g, R"a process the imaginary portions with constants into imaginary signals E"g, E"a. Computing in the respective stages takes place with polynomials the constants of which are determined by resorting to actual measurements of the real and imaginary parts of the dielectric constants of sample cigarettes. Output signals E'g and E'a which correspond to the real parts are transmitted to an adding or summing circuit or stage A'd, and the imaginary parts E"g and E"a are transmitted to a second adding or summing circuit A"d. The added signals ∈' provide the real part of the dielectric constant (at the output of the circuit or stage A'd) and the added signals ∈" provide the imaginary part of the dielectric constant (at the output of the circuit or stage A"d). The reference character V denotes in FIG. 6 a conventional circuit which furnishes a complex value ∈ on the basis of the values 6'∈ and ∈".

A correction stage or circuit (corresponding to the stage Kg shown in FIG. 5) can be utilized to furnish, when necessary, empirically determined correction signals. The value of the complex dielectric constant ∈ can be ascertained (in V) by vectorial addition of the values ∈' and ∈".

Figure 8:
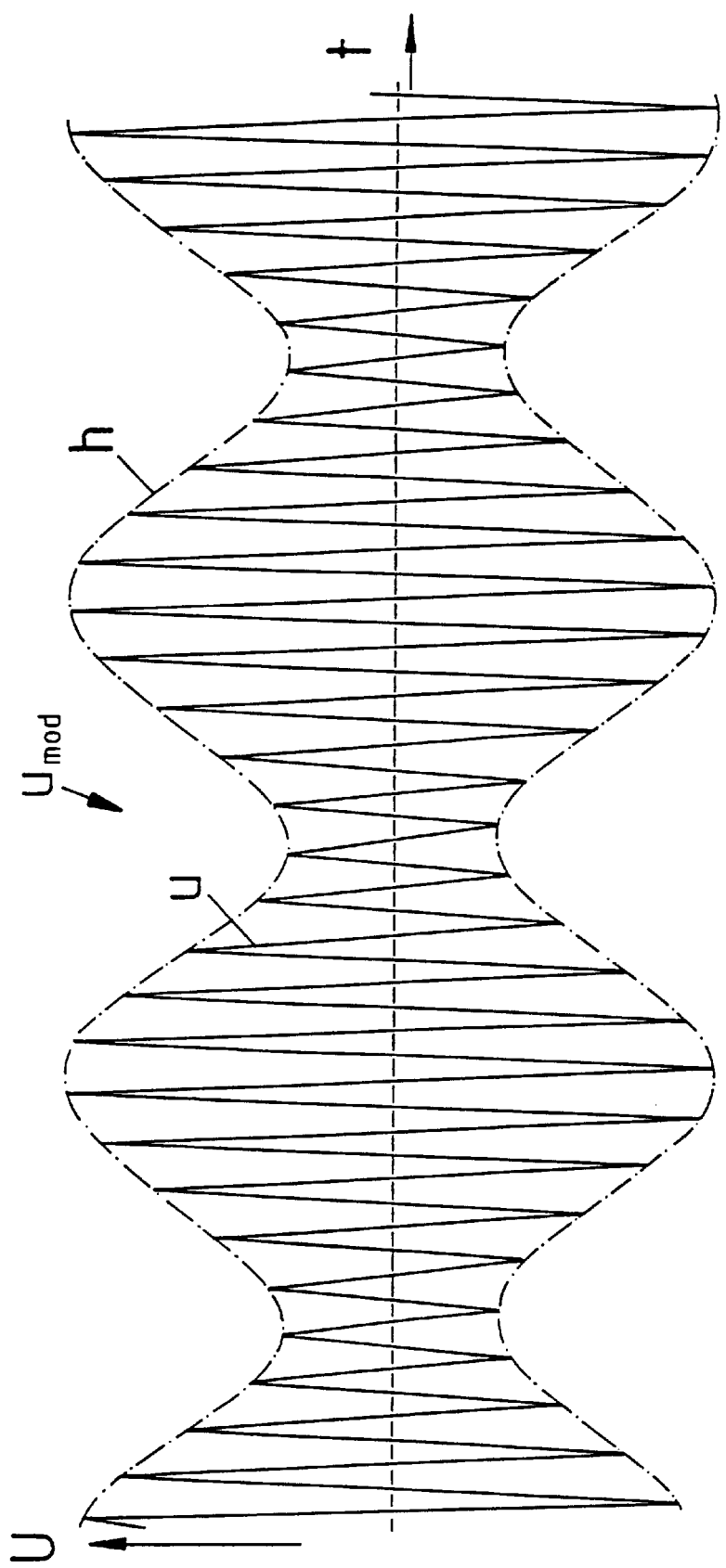
FIG. 8 is a coordinate system showing a modulated microwave signal.

FIGS. 7, 8 and 9 illustrate certain features of a further apparatus employing a microwave generator 3 for the transmission of microwaves, preferably in the GHz range (for example, approximately 6 GHz). The signal from the generator 3 is transmitted as carrier frequency to a modulating circuit 36 wherein the microwave signal is amplitude modulated with at least one substantially sinusoidal signal having a considerably lower frequency and being transmitted by a sender 37. A modulator which can be utilized at 36 in the apparatus of FIG. 7 to generate a secondary frequency signal by resorting to amplitude modulation is known as Module MDC-177 and is distributed by the Firm Adams Russel, Anzac Division, 80 Cambridge Street, Burlington, Md.

A specific example of an acceptable modulating circuit 36 is as follows: 5.8 GHz modulated with 10 MHz provides 5.790 GHz and 5.810 GHz. A similar or identical component part can be utilized in the apparatus of FIG. 10 as a mixer 47 to effect a downward mixing of the GHz frequency. Example: The characteristic frequencies of 5.790 GHz and 5.810 GHz mixed with 5.7850 GHz provide 25 MHz and 45 MHz.

The progress of an amplitude modulated microwave signal Umod is shown in the coordinate system of FIG. 8 as a function of time t. It comprises high-frequency microwave oscillations u of the generator 3 and the superimposed modulating oscillation which forms a substantially sinusoidal envelope curve h. The amplitude modulated microwave signal is transmitted, by way of the circulator 18 shown in FIG. 7, to a resonator arrangement 1 and the high-frequency signals furnished by the output means of the arrangement 1 are caused to pass through a further circulator 19 to the input e of a signal splitting or dividing circuit 38, e.g., a circuit of the type known as Type HP Power Splitter 116678 distributed by the Firm Hewlett-Packard, Herrenberger Strasse 130, D-71034 Böblingen, Federal Republic Germany. As shown in FIG. 9, the amplitude modulated signal furnishes (in the embodiment of FIG. 7) three frequency bands, namely a basic frequency band f2 and two auxiliary or secondary frequency bands f1 and f3. As concerns the resonance curve, the basic frequency band f2 for an empty resonator arrangement 1 is preferably selected in such a manner that it is located at the inversion point Uw of the resonance curve uo. The corresponding signals U1, U2 and U3 on the resonance curve u of signals which are damped by a substance in the resonator arrangement 1 (the resonance frequency of the curve u has been shifted due to the presence of the filler 12b in the arrangement 1) are ascertained in that an input signal furnished to the input e of the signal dividing circuit 38 is split into three signals which are transmitted by the outputs a, b, c of the circuit 38 to three filters 39a, 39b, 39c, respectively. These filters are set up in such a manner that each thereof permits the passage of a signal of a frequency band f1, f2, f3. For example, the filters 39a, 39b, 39b can be of the type known as MAX 274 distributed by Maxim Integrated Products, 120 San Gabriel Drive, Sunnyvale, Calif. 94086. The outputs of the filters 39a, 39b, 39c are respectively connected to the inputs of diodes 22a, 22b, 22c which transmit d-c signals, and such signals are digitalized by the respective ones of three A/D converters 41a, 41b, 41c. The outputs of the converters 41a, 41b, 41c are connected to the respective inputs of the evaluating or processing circuit 11 of FIG. 7.

In principle, it suffices to process two of the three ascertained signals (such as the signals U1, U2 or U1, U3 or U2, U3) of the damped resonance curve u for the ascertainment of the wet mass or dry mass. However, it is also possible to carry out such determination by resorting to three signals. Furthermore, it is possible to form by modulation more than two auxiliary or secondary bands and to thereupon evaluate the corresponding signals.

The apparatus of FIG. 7 can be modified in such a way that the average frequency f2 is not located at a flank of the resonance curve u (see FIG. 9) but rather at its apex, i.e., at fo. In such apparatus, the auxiliary or secondary frequencies f1 and f2 are symmetrical thereto so that the corresponding signals U1, U3 can be evaluated in a manner to be described with reference to FIG. 10.

The apparatus of FIG. 10 also employs a generator 3 which transmits microwave signals in the GHz frequency range. A modulator 36 is provided to modulate the signals from the generator 3 in a manner as already described with reference to FIGS. 5 and 6; the input a of the circuit 36 receives a modulating signal from a suitable source. The circuit 36 transmits several microwave signals having frequencies which are closely adjacent each other. Such signals are amplified at 46 and are transmitted to the input of the resonator arrangement 1. As already described with reference to FIGS. 1 and 2, the microwave signals which are being transmitted to the input of the resonator arrangement 1 are symmetrical to the resonance frequency for the idle (empty) resonator arrangement 1. Basically, it is equally possible to employ two microwave generators in lieu of the single generator 3 of FIG. 10, and each discrete generator transmits microwave signals at a selected frequency other than the frequency of the signals transmitted by the other generator. The decoupling can take place in the same manner as described, for example, with reference to FIG. 1, i.e., by resorting to circulators 18 and 19 (not shown in FIG. 10).

The microwave signals are influenced by the presence of tobacco (such as shredded and/or otherwise cut tobacco particles in the filler 12b of a cigarette rod 12) in the resonator arrangement 1 of FIG. 10, and the high frequencies of the thus influenced microwave signals are considerably reduced in the aforementioned mixer 47 having an input a for the reception of a suitable signal. Two selected characteristic signals having considerably lower frequencies are transmitted to the diodes 22a, 22b by way of the respective filters 39a, 39b. The d-c signals at the outputs of the diodes 22a, 22b are digitalized in the corresponding A/D converters 41a, 41b, and the thus obtained signals are transmitted to the corresponding inputs of the evaluating circuit 11. The lowering of frequencies renders it possible to employ simpler and sharper filters for the selected frequency bands.

Signals which are transmitted by the microwave diodes (such as the diodes 22a–22c of FIG. 7 or the diodes 22a, 22b of FIG. 10) are influenced by the temperature of the tested material (such as tobacco). In accordance with the invention, such influence of the temperature can be compensated for by ascertaining the temperature of the tested substance in any well known manner (for example, by employing a temperature sensor in the resonator arrangement 1). It is also possible to utilize a temperature sensor upstream of the resonator arrangement 1, for example, in that part of a cigarette making machine or production line where the cigarette rod 12 or the rod-like filler 12b is formed (an example of such part of a production line is the so-called distributor or hopper of a cigarette maker). It is also possible to employ an infrared radiation thermometer which is trained upon the ends of cigarettes obtained as a result of severing of the cigarette rod 12 at regular intervals to turn out plain cigarettes of unit length or multiple unit length. The thus obtained signals are utilized to compensate for the influence of the temperature of the tested substance upon the diode or diodes.

The resonator arrangement 1 can be heated to an appropriate temperature to avoid the condensation of water.

In accordance with still another feature of the invention, a drift of the measuring or monitoring system can be compensated for by resorting to reference diodes or, if necessary, by utilizing an additional resonator arrangement. For example, the apparatus can employ two resonator arrangements having identical or substantially identical housings and a discrete dielectric resonator in each housing. The inputs of such discrete resonator arrangements are connected to suitable means (such as one or more microwave generators 3) for supplying microwave signals.

Still further, it is within the purview of the invention to employ a resonator arrangement wherein the closed or substantially closed metallic housing (such as the housing 2 of the arrangement 1 shown in FIG. 1) is replaced with an open housing having at least one part (e.g., of a ceramic material) which is permeable to microwaves. Microwaves can penetrate through such permeable part to enter into a flow or another body of a substance to be tested, e.g., a flow of shredded and/or otherwise comminuted tobacco leaves. An advantage of such resonator arrangements is that they can be utilized for the ascertainment of one or more characteristics of a substance which need not be confined in an envelope (such as the tubular wrapper 12a of the cigarette rod 12 shown in FIG. 1). The non-confined substance can be tested to ascertain one or more characteristics, such as the mass/density and/or the moisture content and/or the dielectric constant of tobacco or other flowable substances.

An advantage of the improved method and apparatus is that they permit rapid and accurate determination of various characteristics of numerous semiconducting substances, such as tobacco, particularly the wet mass and/or dry mass and/or dielectric constant.

Figure 11:
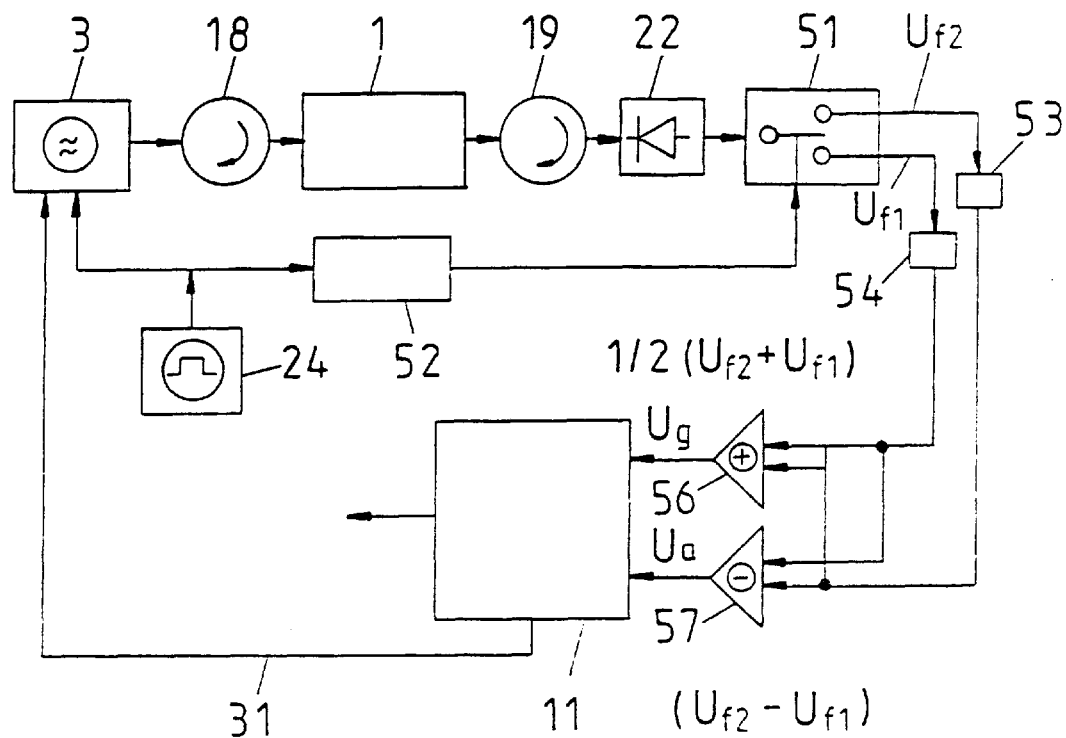
FIG. 11 is a diagrammatic view similar to that of FIG. 1 but showing the details of a further presently preferred apparatus.

FIG. 11 shows a further apparatus wherein the frequency of an output signal furnished in the gigahertz range (e.g., about 6 GHz) by a microwave generator 3 is periodically shifted between two values by a frequency regulator circuit 24. For example, one can employ a rectangular a-c voltage of approximately 100 KHz. This can be seen in FIG. 12a which illustrates changes of the frequency f as a function of time t. The median or average frequency fm is periodically varied within a frequency range Δf in accordance with a rectangular curve s, namely between a higher value f2 and a lower value f1.

The output signals which are transmitted by the microwave generator 3 are supplied to a circulator 18 which prevents a feedback of the output signals and transmits such signals to a high-frequency (HF) resonator arrangement 1, e.g., an arrangement of the type shown in and already describe with reference to FIG. 1. It is assumed that the resonator arrangement 1 of FIG. 11 confines a length of a continuous cigarette rod, e.g., a rod of the type shown in FIG. 1 (as at 12). Such rod comprises a tubular envelope surrounding a compacted rod-like filler of smokable material. However, it is equally possible to employ the high-frequency resonator arrangement 1 of FIG. 11 as a means for monitoring one or more characteristics of another substance, e.g., of filter material for tobacco smoke such as a rod-like filler of synthetic fibrous material within a tubular wrapper of paper, artificial cork or the like. The details of the resonator arrangement 1 of FIG. 1 can match those of the similarly referenced resonator arrangement of FIG. 1.

Figure 12C:
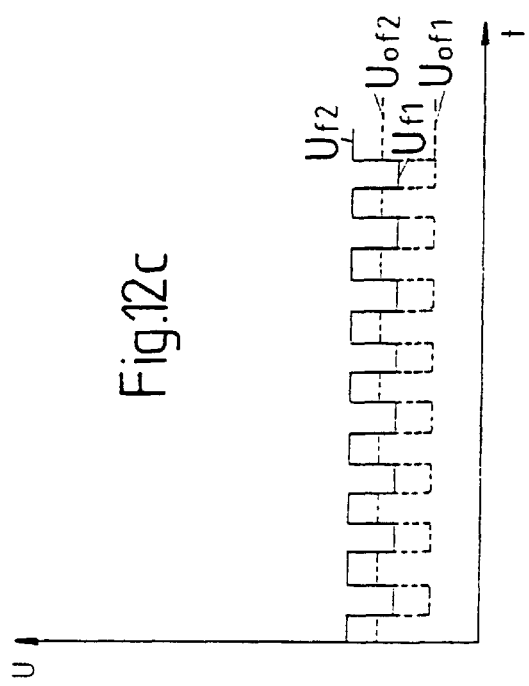
FIGS. 12a, 12b and 12c illustrate coordinate systems wherein the curves denote the high-frequency signals transmitted by the resonator arrangement in the apparatus of FIG. 11.
Figure 12B:
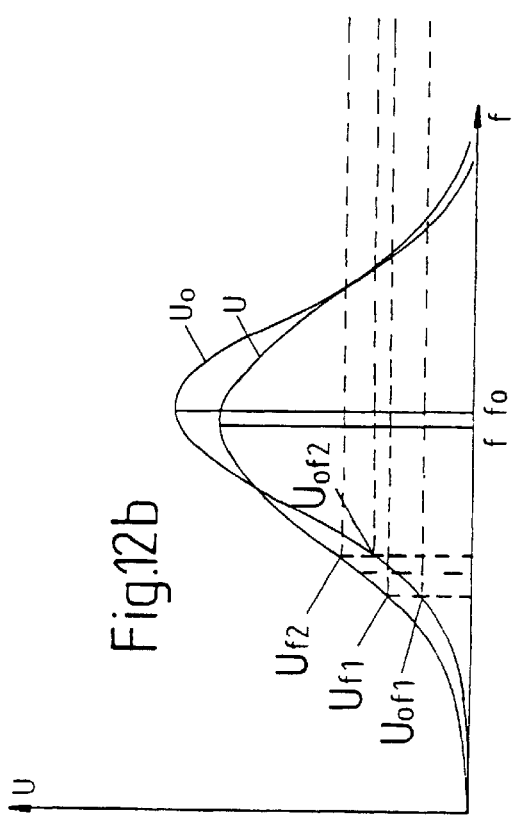
Figure 12A:
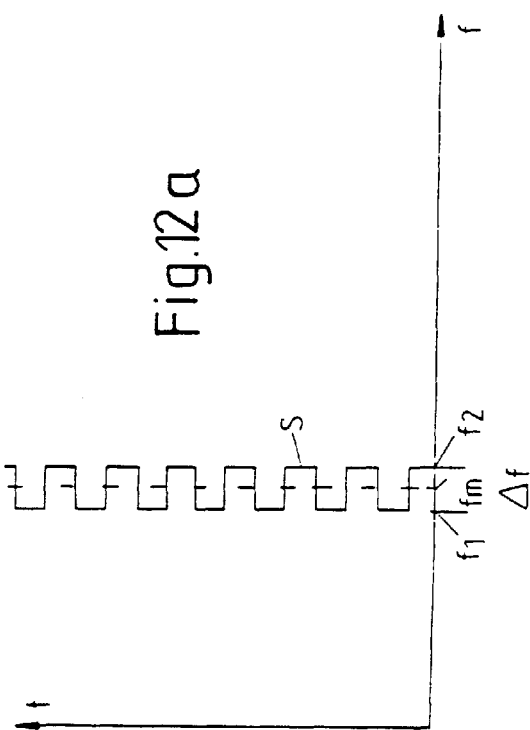

As shown in FIGS. 12a and 12b, the average or median frequency fm of the signals denoted by the rectangular curve s of FIG. 12a is preferably located at the inversion point of the resonance curve uo which was ascertained in the resonator arrangement 1, in the absence of tobacco or filter material, for different frequencies of the supplied microwaves (from the source 3 via circulator 18). The progress of the resonance curve s (when the resonator arrangement 1 confines a portion of an advancing tobacco stream 12 shown in FIG. 1) is shown in FIG. 12b. The resonance frequency when the resonator arrangement 1 is not being traversed by a continuous rod of confined tobacco or tobacco smoke filtering material is denoted by the curve uo of FIG. 12b, and the curve u denotes how the resonance frequency f1 develops when the resonator arrangement 1 is actually traversed by a continuous wrapped filler of tobacco, filter material for tobacco smoke or the like. The resonance frequency fo develops when the resonator arrangement 1 is empty, and the resonance frequency f develops when a wrapped rod-like filler (such as 12 in FIG. 1) is caused to pass through the resonator arrangement 1.

The lower frequency value f1 on the rectangular curve s in the coordinate system of FIG. 12a corresponds to the value denoted by the point Uof1 on the resonance curve uo (resonator arrangement 1 empty) of FIG. 12b, and to the value denoted by the point Uf1 on the resonance curve u (resonator arrangement 1 confining a length of an axially advancing cigarette rod 12) of FIG. 12b. The upper frequency value f2 of the rectangular curve s shown in FIG. 12a corresponds to the values respectively denoted by the points Uof2 and Uf2 on the curves uo and u of FIG. 12b. The values Uf1, Uf2, Uof1 and Uof2 are also shown in the coordinate system of FIG. 12c.

The output signals of the resonator arrangement, namely the resonance signals at the lower modulation value (f1) and the higher modulation value (f2), are transmitted to a resonance diode 22 by way of a second circulator 19 which prevents a feedback to the resonator arrangement 1. The diode 22 can be of the character known as Type HP/8472 B available at Hewlett-Packard. The purpose of the diode 22 is to convert the incoming microwave signal into a d-c signal. The d-c signal is transmitted to a sensor 51 in response to signals from a synchronizer 52 whose operation is a function of the rectangular a-c voltage supplied by the frequency regulator 24. The regulation is carried out in such a way that the voltage values of the resonator arrangement 1 are addressed at the exact instants when the microwave generator 3 furnishes to the resonator arrangement 1 microwaves with the higher (f2) or lower (f1) frequency values of the rectangular curve s.

The above outlined mode of operation ensures that one can obtain the values Uf2 and Uf1 (FIGS. 12b and 12c) which are respectively stored in short-term memories 53 and 54. The output signals of the memories 53 and 54 are transmitted to a summing circuit 56 and to a subtracting circuit 57. The circuit 56 establishes the value ½(Uf2+Uf1)=Ug, and the circuit 57 establishes the value (Uf2−Uf1)=Ua (see also FIG. 12c). The signals or values Ug and Ua are transmitted to the corresponding inputs of the evaluating arrangement 11 the details of which are illustrated in FIG. 13 and which serves to ascertain, for example, the density/mass or the moisture content of a continuously moving body of a substance, e.g., a rapidly advancing cigarette rod containing a rod-like tobacco filler within a tubular wrapper of cigarette paper or the like.

A specially designed circuitry can be provided to ensure that the microwave generator 3 receives a correction signal from the evaluating arrangement 11 via conductor means 31 as soon as the average frequency fm (FIG. 12a) migrates beyond the inversion point of the resonance curve uo. The correction signal which is transmitted via conductor means 31 ensures that the frequency fm at the output of the microwave generator 3 is caused to reassume the value corresponding to the inversion point of the resonance curve uo.

Figure 13:
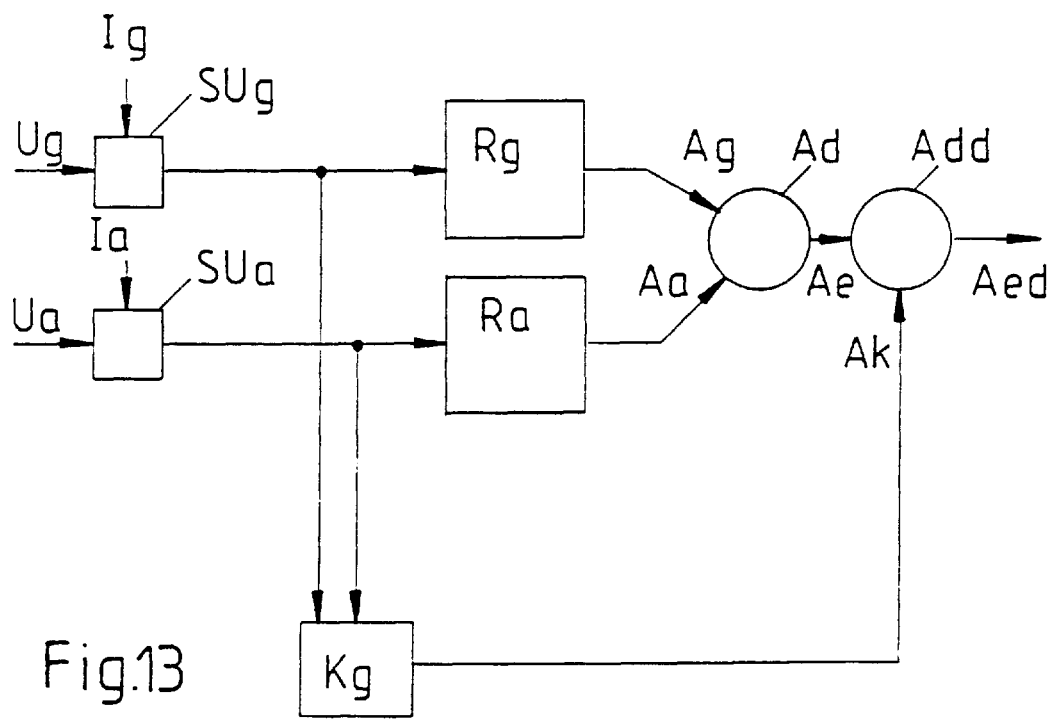
FIG. 13 is a diagrammatic view of an evaluating circuit which can be utilized in the apparatus of FIG. 11.

The manner in which the signals Ua and Ug are processed in the evaluating arrangement 11 of FIG. 1 in order to ascertain the mass/density value of the rod-like tobacco filler is shown in FIG. 13. The first step involves storing the signals Ua and Ug in digitalized form in memories SUa and SUg. A readout device is provided to address the memories SUg and SUa in a sequence corresponding to selected movements of the cigarette rod passing through the resonator arrangement 1 of FIG. 11. For example, each such movement can have a length of 1 mm. Thus, if the cigarette rod is transported through the resonator arrangement at a speed which is required to produce 10000 cigarettes (each having a length of 60 mm) per minute, the scanning frequency is in the range of 100 microseconds. In other words, the information which is stored in the memories SUg and SUa is addressed at a frequency of 100 microseconds. The pulses Ig and Ia for the transmission of such information to calculating stages Rg and Ra are even shorter than 100 microseconds, and the stages Rg and Ra process the incoming signals together with constants to furnish output signals Ag and Aa entering the corresponding inputs of a first summing or adding stage Ad. In a simple case, the calculation in the stages Rg and Ra can be carried out with polynomials of the type a+b Ug=AG and c+d Ua=Aa. The constants a, b, c and d are ascertained by resorting to parameterization involving a weighing of cigarettes to determine the exact values of mass/density and the related values of Ug and Ua. The relationships between various densities/masses and the corresponding values of Ug and Ua permit a determination of the constants a to d.

In principle, it is equally possible to employ higher-order polynomials and/or other functions.

The output signals Ag and Aa are transmitted (by the calculating stages Rg and Ra) to the first summing or adding stage Ad which transmits an output signal Ae denoting the mass/density of the monitored substance. If the output signal Ae deviates from the exact (e.g., measured) value of the mass/density, one can employ a correction stage Kg which transmits an empirically ascertained correction signal Ak to a second adding or summing stage Add which further receives output signals Ae from the first summing or adding stage Ad. The output signal Aed of the second stage Add is even more accurately representative of the mass/density of the tested substance.

The principle of testing a substance (such as a tobacco rod) in order to ascertain the moisture content is the same as described above in connection with the determination of mass/density. The aforediscussed parameterization then involves resort to cigarettes having known but different moisture contents. In other words, the weights of cigarettes are used in conjunction with a determination of density/mass, and the moisture contents are resorted to when the method and apparatus of the invention are to ascertain the moisture content of successive increments of a running continuous cigarette rod.

An advantage of the method described hereinbefore with reference to FIGS. 11 to 13 is that the two values of the rectangular modulation oscillation can be more readily maintained in a stable condition than a sinusoidal vibration. Additional advantages are achieved in connection with the evaluating signals which are generated as a result of modulation.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art of ascertaining the characteristics of tobacco or other substances and, therefore, such adaptations should and are intended to be comprehended within the meaning and range of equivalence of the appended claims.

What is claimed is:

1. A method of ascertaining at least one characteristic of a substance by means of a high-frequency resonator arrangement which is detuned in the presence of the substance, comprising the steps of supplying to an input of the resonator arrangement microwaves having two different frequencies by repeatedly shifting the frequency between high and lower frequency values, said resonator arrangement being operable to produce first and second curves of high-frequency output signals in the presence and absence of a substance, respectively, said curves having different amplitudes at said different frequencies; and evaluating said output signals including comparing the amplitudes of at least said first curve at said different frequencies to ascertain the relative damping of said output signals at said different frequencies due to the presence of a substance to thereby ascertain a characteristic of said substance.

2. The method of claim 1, wherein said supplying step includes continuously transmitting to the input microwaves having two different frequencies.

3. The method of claim 1, further comprising the step of periodically varying the frequencies of microwaves supplied to the input of the resonator arrangement.

4. The method of claim 3, wherein said varying step includes repeatedly and continuously wobbling between higher-frequency and lower-frequency values.

5. The method of claim 4, wherein said microwaves have frequencies each allocated to a sloping flank of a curve.

6. The method of claim 1, wherein the substance is tobacco and said at least one characteristic is the mass/density of tobacco.

7. The method of claim 1, wherein the substance is tobacco in a tobacco particle flow and said at least one characteristic is the moisture content/mass of tobacco.

8. The method of claim 1, wherein the substance is tobacco in a flow of shredded tobacco particles and said at least one characteristic is the dielectric constant of shredded tobacco.

9. Apparatus for ascertaining at least one characteristic of a substance, comprising a resonator arrangement; means for supplying to an input of said arrangement microwave signals at two different frequencies, said arrangement having output means for the transmission of first and second high-frequency output signals generated in the presence and in the absence of a substance, respectively, at said arrangement; and means for evaluating said first high-frequency output signal at said two different frequencies, said evaluating means comprising means to mathematically combine said output signals at said two frequencies with constants to generate signals representing a characteristic of said substance.

10. The apparatus of claim 9, wherein said supplying means includes at least one microwave generator arranged to uninterruptedly transmit to said input microwave signals at said two different frequencies.

11. The apparatus of claim 10, wherein said generator includes means for periodically altering the frequency of said microwave signals.

12. The apparatus of claim 9, wherein said supplying means comprises a microwave generator connected to said input and a frequency regulator connected with said generator to periodically vary the frequency of signals from said generator between higher and lower values.

13. The apparatus of claim 9, wherein said supplying means comprises a microwave generator connected to said input and a frequency regulator connected with said generator to continuously and regularly vary the frequency of signals from said generator between higher and lower values.

14. The apparatus of claim 9, wherein said supplying means comprises a microwave generator connected to said input and a frequency regulator connected with said generator to continuously and regularly vary the frequency of signals from said generator between higher and lower values, said microwave signals both being higher or lower than the resonance frequency of said resonator arrangement.

15. The apparatus of claim 9, wherein said supplying means includes means for transmitting to said input microwaves at frequencies having upper and lower threshold values and continuously wobbling between said values, said values being at least substantially symmetrical with reference to an inversion point of a downwardly sloping flank of a resonance curve.

16. The apparatus of claim 9, wherein said supplying means includes means for continuously transmitting to said input microwave signals at two different frequencies, and further comprising means for scaling down the high-frequency signals between said output means and said evaluating means and means for selectively filtering, between said scaling down means and said evaluating means, those frequency ranges which influence said shifts of resonance frequencies and said damping of the resonance curves by a substance.

17. The apparatus of claim 9, wherein said arrangement comprises a metallic housing having an inlet and an outlet for a flow of a substance to be tested, such as a tobacco stream.

18. The apparatus of claim 17, wherein said housing is dynamically balanced.

19. The apparatus of claim 18, wherein said housing includes a cylinder.

20. The apparatus of claim 17, wherein said arrangement further comprises at least one dielectric resonator in said housing.

21. The apparatus of claim 20, wherein said at least one dielectric resonator provides a path for the advancement of a substance between said inlet and said outlet.

22. The apparatus of claim 21, wherein said arrangement further comprises a tubular guide for the substance, said guide including portions at said inlet and said outlet.

23. The apparatus of claim 22, wherein said guide extends through said at least one dielectric resonator.

24. The apparatus of claim 22, further comprising conductive sleeves surrounding said guide in the regions of said inlet and said outlet.

25. The apparatus of claim 24, wherein said sleeves contain a metallic material.

26. The apparatus of claim 9, wherein said arrangement comprises two resonators each receiving microwave signals from said supplying means, one of which transmits said high-frequency signals, and the other of which transmits to said evaluating means additional signals influenced by a reference substance to compensate for disturbances.

27. The apparatus of claim 26, wherein said arrangement further comprises at least substantially identical housings for said resonators.

28. The apparatus of claim 9, wherein said at least one characteristic is density/mass of tobacco.

29. The apparatus of claim 9, wherein said at least one characteristic is the moisture content of cut tobacco in a cigarette rod.

30. The apparatus of claim 9, wherein said at least one characteristic is the dielectric constant of cut tobacco, particularly in a cigarette rod.

31. A method of ascertaining at least one characteristic of a substance by means of a high-frequency resonator arrangement which is detuned in the presence of the substance, comprising the steps of supplying to an input of the resonator arrangement microwaves having two frequencies by repeatedly shifting the frequency between higher and lower values, the resonator arrangement being operable to generate at an output first and second curves of high-frequency output signals in the presence and absence of a substance, respectively, said output signals having different amplitudes at said two frequencies; and evaluating said output signals including providing a further signal denoting the sum of said amplitudes, processing said further signal into a signal denoting the average of said amplitudes, providing an additional signal denoting the difference between said amplitudes, and transmitting said further and additional signals to calculating stages, and mathematically combining said further and additional signal with constants in said calculating stages to generate signals representing a characteristics of said material.

32. The method of claim 31, further comprising the step of periodically varying the frequencies of microwaves supplied to the input of the resonator arrangement, said varying step including repeatedly switching between higher and lower frequency values.

33. The method of claim 31, further comprising the step of modulating the frequencies of said microwaves with a lower-frequency rectangular a-c voltage.

34. The method of claim 33, wherein said output signals are d-c signals and said modulated frequencies have maximum and minimum values, and further comprising the steps of ascertaining the d-c signals which are transmitted by the output of the resonator arrangement at said minimum and maximum values of said modulated frequencies, and processing the thus ascertained maximal and minimal signals into evaluation signals.

35. The method of claim 17, further comprising the step of ascertaining said constants by parameterization on the basis of to-be-ascertained reference values of the substance.

36. The method of claim 35, wherein said reference values include the density/mass, moisture content and dielectric constant.

37. The method of claim 31, wherein said substance is tobacco and said at least one characteristic is the mass/density of tobacco.

38. The method of claim 37, wherein said substance is a rod-like filler of cut tobacco.

39. The method of claim 31, wherein said substance is tobacco and said at least one characteristic is the moisture content of tobacco.

40. The method of claim 39, wherein said substance is a rod-like filler of cut tobacco.

41. Apparatus for ascertaining at least one characteristic of a substance, comprising a resonator arrangement; means for supplying to an input of said arrangement microwave signals at two different frequencies, said arrangement having output means for the transmission of high-frequency output signals at said two frequencies generated in the presence of a substance at said arrangement; and evaluating means for evaluating said output signals, said evaluating means comprising summing and subtracting circuits for summing and subtracting said output signals, to produce sum and difference signals, and calculating stages for mathematically combining said sum and difference signals, respectively, with constants to determine first and second calculated output signals, and means for adding said calculated output signals.

42. The apparatus of claim 41, wherein said supplying means comprises a microwave generator connected to said input and a frequency regulator connected with said generator to periodically vary the frequency of signals from said generator between higher and lower values.

43. The apparatus of claim 41, further comprising means for modulating the frequencies of microwaves with a lower-frequency rectangular a-c voltage.

44. The apparatus of claim 43, wherein the first and second high-frequency signals are d-c signals and the modulated frequencies have maximum and minimum values, and further comprising means for ascertaining the d-c signals which are transmitted by the output means of the resonator arrangement at said minimum and maximum values of said modulated frequencies, and means for evaluating the ascertained d-c signals into evaluation signals.

45. The apparatus of claim 27, wherein said evaluating means further comprises means for ascertaining said constants by parameterization on the basis of reference values of a substance, said reference values including—as a function of the at least one characteristic to be ascertained—at least one of the density/mass, moisture content and dielectric constant of the substance.

46. The apparatus of claim 41, wherein said resonator arrangement comprises a metallic housing having an inlet and an outlet for the flow of a substance to be tested, such as a tobacco stream.

47. The apparatus of claim 46, wherein said housing is dynamically balanced.

48. The apparatus of claim 47, wherein said housing includes a cylinder.

49. The apparatus of claim 46, wherein said arrangement further comprises a least one dielectric resonator in said housing.

50. The apparatus of claim 41, wherein said at least one characteristic is density/mass of tobacco.

51. The apparatus of claim 41, wherein said at least one characteristic is the moisture content of cut tobacco in a cigarette rod.

* * * * *